United States Patent [19]
McCarver

[11] Patent Number: 5,349,965
[45] Date of Patent: Sep. 27, 1994

[54] SURGICAL FLUID EVACUATION SYSTEM

[75] Inventor: Stacey G. McCarver, Marietta, Ga.

[73] Assignee: Kimberly-Clark Corporation, Neenah, Wis.

[21] Appl. No.: 169,723

[22] Filed: Dec. 17, 1993

Related U.S. Application Data

[63] Continuation of Ser. No. 808,131, Dec. 16, 1991, abandoned.

[51] Int. Cl.5 .......................... A61F 5/37; A61B 19/00
[52] U.S. Cl. ...................................... 128/846; 128/849
[58] Field of Search ............................... 128/849–856, 128/846; 604/369, 374, 378, 385.1; 206/204; 119/1, 156

[56] References Cited

U.S. PATENT DOCUMENTS

| | | | |
|---|---|---|---|
| 826,978 | 7/1906 | Whittington | 5/604 |
| 3,650,267 | 3/1972 | Anderson | 128/132 |
| 3,668,050 | 6/1972 | Donnelly | 128/849 |
| 3,677,266 | 7/1972 | Green | 128/853 |
| 3,763,857 | 10/1973 | Schrading | 128/853 |
| 3,902,484 | 9/1975 | Winters | 128/849 |
| 4,323,062 | 4/1982 | Canty | 128/132 D |
| 4,414,968 | 11/1983 | Amin | 128/853 |
| 4,489,720 | 12/1984 | Morris | 128/853 |
| 4,553,539 | 11/1985 | Morris | 128/854 |
| 4,559,937 | 12/1985 | Vinson | 128/853 |
| 4,616,642 | 10/1986 | Martin et al. | 128/132 D |
| 4,635,913 | 1/1987 | Rothman | 269/327 |
| 4,649,861 | 3/1987 | Elkins | 119/156 |
| 4,729,404 | 3/1988 | Hergenroeder | 604/356 |
| 4,730,726 | 3/1988 | Holzwarth | 206/339 |
| 4,852,517 | 8/1989 | Smith | 119/156 |
| 4,873,997 | 10/1989 | Marshall | 128/849 |
| 4,923,453 | 5/1990 | Bullard | 604/356 |
| 4,936,318 | 6/1990 | Schoolman | 128/849 |
| 4,960,136 | 10/1990 | Linnemann et al. | 128/845 |
| 4,974,604 | 12/1990 | Morris | 128/853 |
| 5,002,069 | 3/1991 | Thompson | 128/853 |
| 5,095,918 | 3/1992 | Busch | 128/849 |
| 5,161,544 | 11/1992 | Morris | 128/849 |

FOREIGN PATENT DOCUMENTS

| | | |
|---|---|---|
| 45015 | 12/1931 | Denmark . |
| 0412213 | 2/1991 | European Pat. Off. . |
| 2650501 | 2/1991 | France . |

Primary Examiner—Michael A. Brown
Attorney, Agent, or Firm—Patrick C. Wilson

[57] ABSTRACT

Disclosed herein is a fluid evacuation system which is particularly well-suited for removing liquids from the site of a surgical procedure. In one configuration the system is in the form of a pad which can be placed directly on a patient or used in conjunction with a surgical drape. The pad is connected to a vacuum source and as fluids flow across the top surface of the pad, they are drawn down into a fluid receiving chamber and then removed via a suction line. As a result, fluids present during a surgical procedure are taken completely away from the operating site. In another configuration, the system is in the form of a suction rail which operates in the same fashion but can be molded or formed into a particular shape and then attached to a surgical drape in the expected path of fluid run-off.

16 Claims, 4 Drawing Sheets

SURGICAL FLUID EVACUATION SYSTEM

This application is a continuation of application Ser. No. 07/808,131 entitled "SURGICAL FLUID EVACUATION SYSTEM" and filed in the U.S. Patent and Trademark Office on Dec. 16, 1991, now abandoned.

BACKGROUND OF THE INVENTION

The present invention relates to a means for collecting and removing fluids from the areas adjacent a surgical site during a surgical procedure. More particularly, the present invention relates to a suction pad and a surgical drape incorporating such a suction pad for collecting and evacuating fluids during a surgical procedure.

While traditional surgical procedures have always been bloody, the advent of less invasive surgical procedures, such as knee arthroscopies, has actually increased the total amount of fluids present during a given surgical procedure due to the large quantities of irrigation fluids used. Attempts to control body and other fluids have ranged from simple to increasingly complicated methods. This is due in part to increased concerns over the risks to health care workers in the operating room. This includes the surgical team as well as those individuals responsible for preparing and cleaning the operating room after the completion of a procedure.

Fluid control in the most crude form is characterized by simply letting all fluids fall off the operating field onto the operating room floor followed by a complete clean-up by the housekeeping staff. Several risks are involved in practicing fluid management in this manner. First, all fluids originating in the operative field must fall past the operative staff thereby bringing some degree of risk of contamination to the operating staff themselves due to the contaminants contained within the fluid. This is compounded by the secondary risks of having liquids on the floor with the associated risks of slipping and falling. Thirdly, there are increased risks to the housekeeping staff due to their contact with the fluids during the clean-up procedure.

Absorbent pads are sometimes placed on the operating room floor to capture falling liquids as one solution to this problem. However, these pads have a limited capacity and seldom can be situated so as to capture all the fluid. In any event, most operating room personnel object to floor capture methods as the fluids have already passed by the staff. Furthermore, the contaminated floor pads must still be handled by housekeeping staff during the clean-up procedure.

Another solution to this problem has been the advent of a product commonly referred to as a lily pad which sits on the floor and consists of a hard, plastic platform on which the surgeon and staff can stand during the operative procedure. The lily pad has holes in its upper surface through which fluids are drawn and removed by room suction devices. The problem with this design, however, is the fact the actual removal of the fluid does not take place until the fluid has passed by the operating room staff during the surgical procedure. In addition, lily pads are of a finite size and therefore, if the fluids do not fall directly on the pad, additional clean-up will still be required by the housekeeping staff. Lastly, because of the hard surface of such lily pads, splashing is often a problem.

Rudimentary operative field fluid control is achieved through the use of absorbent materials near the operative site, such as gauze sponges and/or huck towels in and around the operative site. Another solution is the building of absorbent materials into or on the surgical drapes for limited fluid control. Such methods, however, are effective only in those situations where fluid flow is extremely low and/or sporadic. In cases where heavy irrigation is anticipated, the towels will have to be continuously replaced to afford any kind of control for heavy fluid volume.

Another common means of fluid control and removal which is site specific is the use of suction lines. However, such suction devices are very localized in the utilization, are hand held and must be held in place, most often directly adjacent the fluid source to be effective.

Perhaps the greatest advancement in large scale control of fluids is the utilization of fluid collection pouches, either alone, or in conjunction with surgical drape designs. Such fluid collection pouches will often surround at least a portion of the operative site to provide continuous fluid collection. Such fluid collection pouches can optionally be used in conjunction with drain tubes to allow the fluids collected within the pouch to be siphoned off to another reservoir such as a collection pail underneath the operating table. A drawback with such fluid collection pouches, however, is the fact that they depend upon gravity to work. As a result, the pouches oftentimes hang over the side of the patient and operating room table such that they are often bumped into or leaned up against by the operating room staff which in turn can cause spillage of the fluid back out of the bag and/or closing of the opening in the bag so that fluids cannot properly enter.

It is therefore an object of the present invention to provide a fluid containment and removal device which will improve upon the aforementioned designs. It is another object of the present invention to provide a fluid collection and removal device which has virtually unlimited capacity thereby alleviating many of the problems with past designs due to capacity restrictions. It is yet a further object of the present invention to provide a fluid collection and removal system which will yield an operating field directly adjacent the operating site which is relatively clean and free of fluid. These and other objects of the present invention will become more apparent upon a further review of the following specification, drawings and claims.

SUMMARY OF THE INVENTION

The present invention is directed to a fluid evacuation or suction device which can be used to channel and remove fluids from the operating site during a surgical procedure. The system has a liquid impervious bottom layer and a liquid pervious top layer with the top and bottom layers being joined to each other by a fluid impervious seal to define a fluid receiving chamber between the top and bottom layers. Separation means are located within the chamber for maintaining the top and bottom layers generally separated from one another and the chamber itself is provided with means for evacuating the chamber of liquid entering the chamber through the liquid pervious top layer. The system is placed adjacent the operating site or in the general path of fluid run-off. A source of vacuum is connected to the fluid receiving chamber. As fluid is directed across the liquid pervious top layer, it enters the fluid receiving chamber where it then can be drawn-off via the evacuation means.

If desired, the separation means can be made from a liquid permeable material such as an open celled foam so that maximum utilization of the fluid receiving chamber is possible. To insure effective utilization of the system, it may further include one or more liquid control rails located about at least a portion of the periphery of the top layer of the system and extending above the general plane of the top layer for channeling and retaining fluids on the top layer. If desired, the liquid control rails themselves may act as a fluid evacuation system and can be made to be in fluid communication with the fluid receiving chamber so that the liquid control rails themselves may receive fluids.

The liquid-permeable top layer also may be made liquid absorbent so as to collect and retain liquids prior to their passage into the fluid receiving chamber. Consequently, the top layer may include a first layer of liquid absorbent and permeable material in contact with a second layer of perforated polymeric film with the first layer being disposed away from the fluid receiving chamber. In addition, the top layer may have selected areas of liquid permeability and impermeability.

When the system is very large in design and/or the source of vacuum is not strong, the fluid receiving chamber may be compartmentalized into a plurality of chambers each of which has its own evacuation means so that selected fluid evacuation can take place.

The fluid evacuation system may be used by itself or in conjunction with a surgical drape in which case the fluid evacuation system may be placed on top of or physically attached to the drape or patient. In another design, the fluid evacuation system may be formed into a rail-type configuration which can be molded and conformed to form a fluid dam or trough to stop, collect and remove fluids.

DETAILED DESCRIPTION OF THE INVENTION

Figure 1:
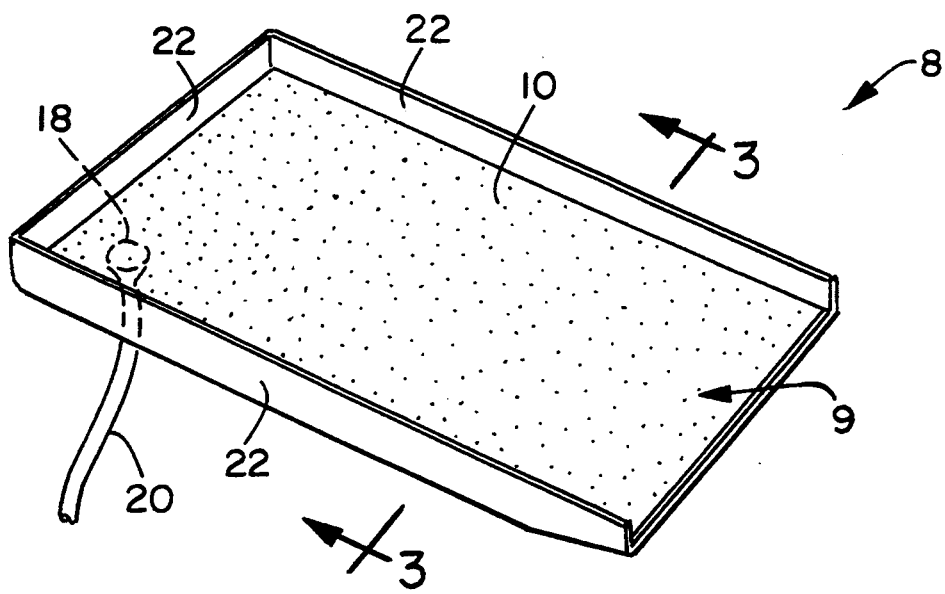
FIG. 1 is a perspective view of a fluid evacuation system according to the present invention. In this embodiment the invention is in the form of a pad.

The present invention is directed to a means for collecting fluids generated and/or released during a surgical procedure in and about the surgical site. The invention comprises a fluid or liquid evacuation system which when connected to a source of vacuum will act to remove the fluids completely away from the operating site as opposed to collecting and retaining them in close proximity to the surgical site as has been typically the case with, for example, fluid collection pouches. Generally speaking, to accomplish this, the system 8 of the present invention uses a liquid pervious top layer 10 and a liquid impervious bottom layer 12 which are sealed about their peripheries 13 to one another to create a fluid receiving chamber 14 which contains separation means 16 to keep the fluid chamber 14 from collapsing when the chamber 14 is placed under negative pressure. Located in at least one portion of the fluid chamber 14 is an evacuation means 18 such as a fluid port which can be attached to a suction hose 20. As liquid flows across the top layer 10, it enters the fluid chamber 14 and is then withdrawn from the fluid chamber 14 via the evacuation means 18.

Figure 2:
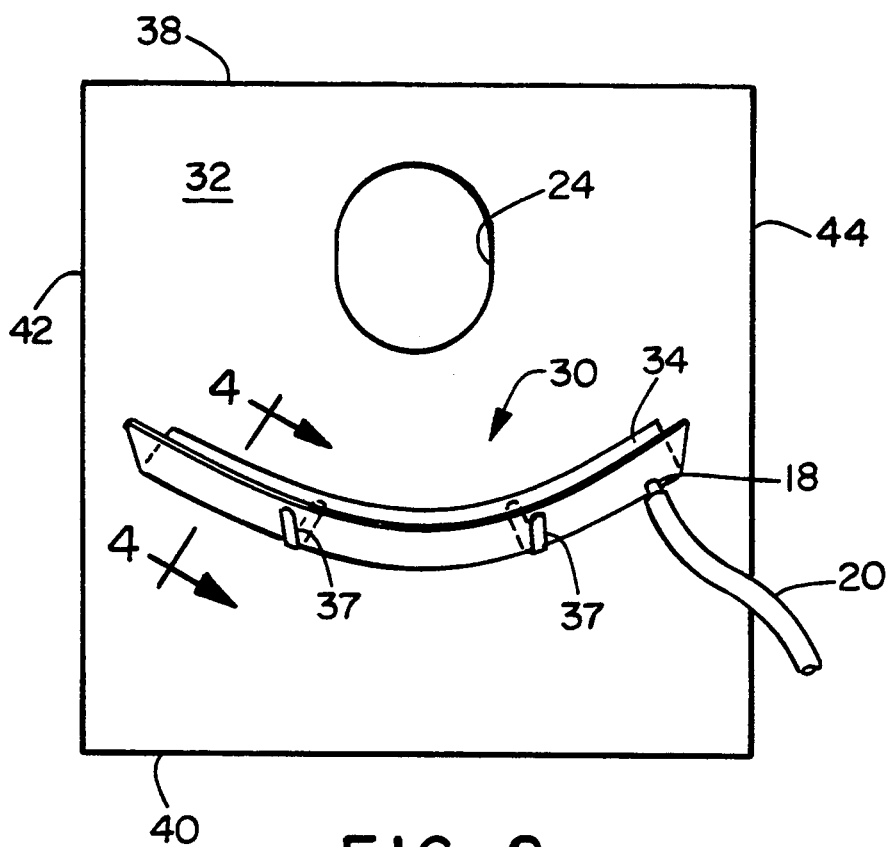
FIG. 2 is a perspective view of a fluid suction rail according to the present invention attached to a surgical drape in the expected path of fluid run-off.
Figure 3:
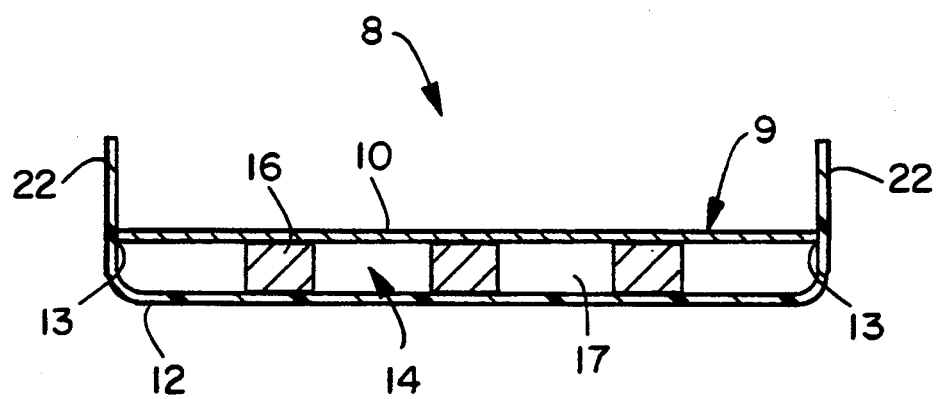
FIG. 3 is a cross-sectional view of the fluid evacuation system of FIG. 1 taken along line 3—3 of FIG. 1.
Figure 4:
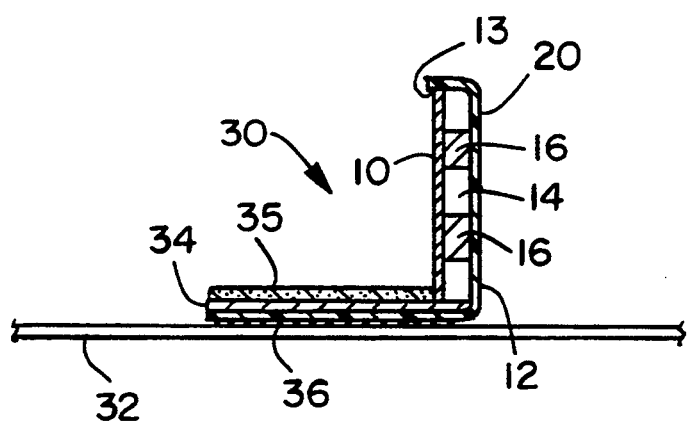
FIG. 4 is a cross-sectional view of the fluid suction rail of FIG. 2 taken along line 4—4 of FIG. 2.

To illustrate the usefulness of the present invention, several embodiments of the invention are shown in FIGS. 1 through 6. In FIGS. 1 and 3, the fluid evacuation system 8 is in the form of a flat pad 9 which may or may not include optional fluid control rails 22 located about the periphery 13 of the system 8 to channel and direct liquids onto the liquid pervious top surface 10. This configuration may be placed in the expected path of fluid run-off to channel, collect and withdraw fluids from the operating site. In FIGS. 2 and 4, the system is shown as a flexible evacuation rail 30 which may be pre-attached to a surgical drape 32 or provided with an adhesive attachment flap 34 so that the system 30 can be sold separately and then molded into shape and attached to the surgical drape 32 where needed.

Figure 5:
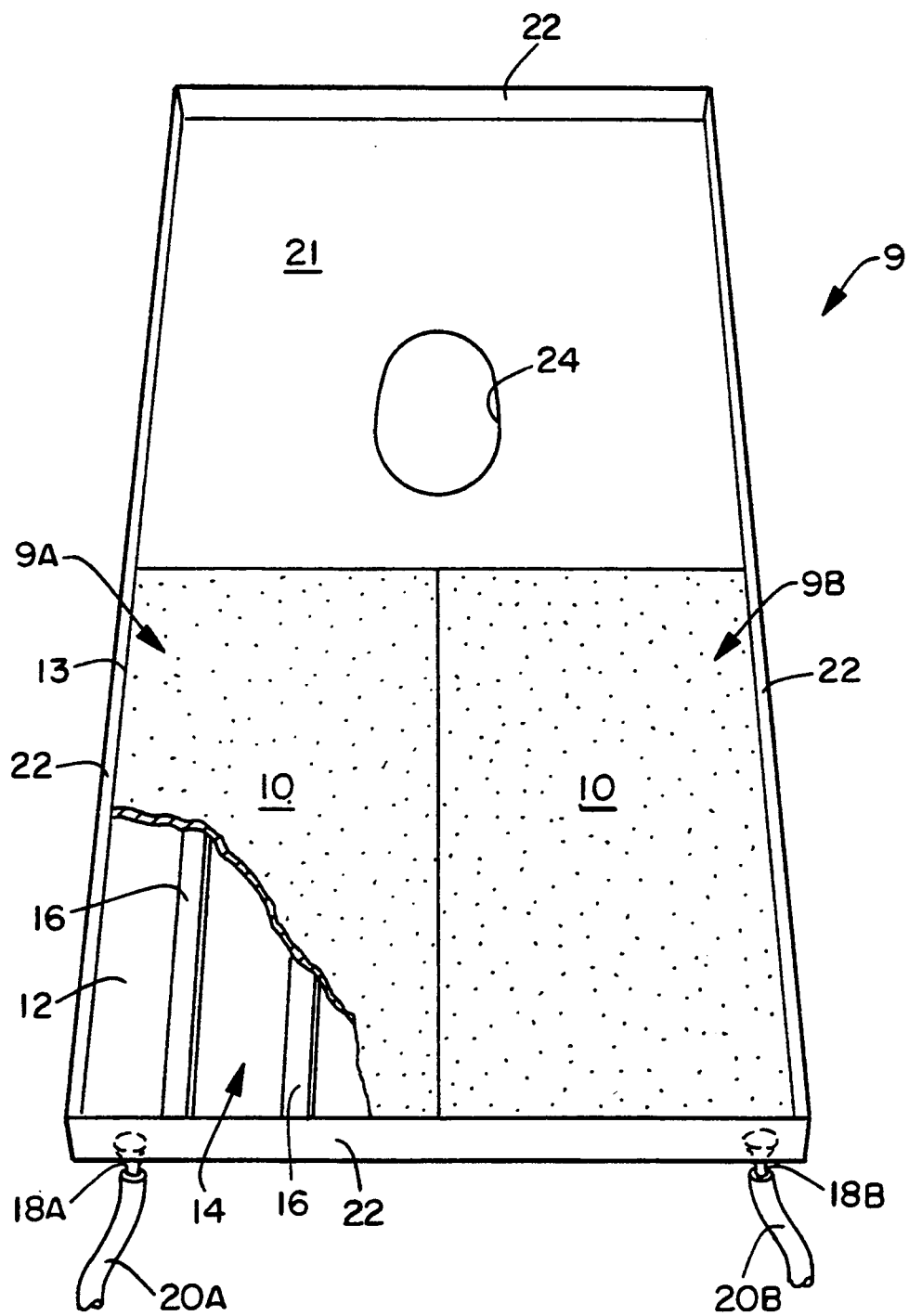
FIG. 5 is a perspective view of yet another fluid evacuation system according to the present invention.

In FIG. 5, the system 8 of the present invention is shown as being in the form of a pad surrounded by optional fluid control rails 22. In this embodiment, the area 21 directly surrounding the fenestration 24 is not provided with a fluid collection chamber 14. However, directly below the fenestration 24 in the path of expected fluid run-off, the pad is provided with at least one and, if desired, multiple fluid collection pads 9A and 9B which each have their own evacuation means 18A and 18B so that selective removal of fluids can be achieved. This embodiment is particularly useful with a vacuum source (not shown) which does not have sufficient vacuum power to create a vacuum throughout the entire structure. As a result, the evacuation tube can be selectively attached to a specific fluid receiving chamber or all the fluid receiving chambers can be connected to an evacuation source if so desired and if there is sufficient vacuum force.

Figure 6:
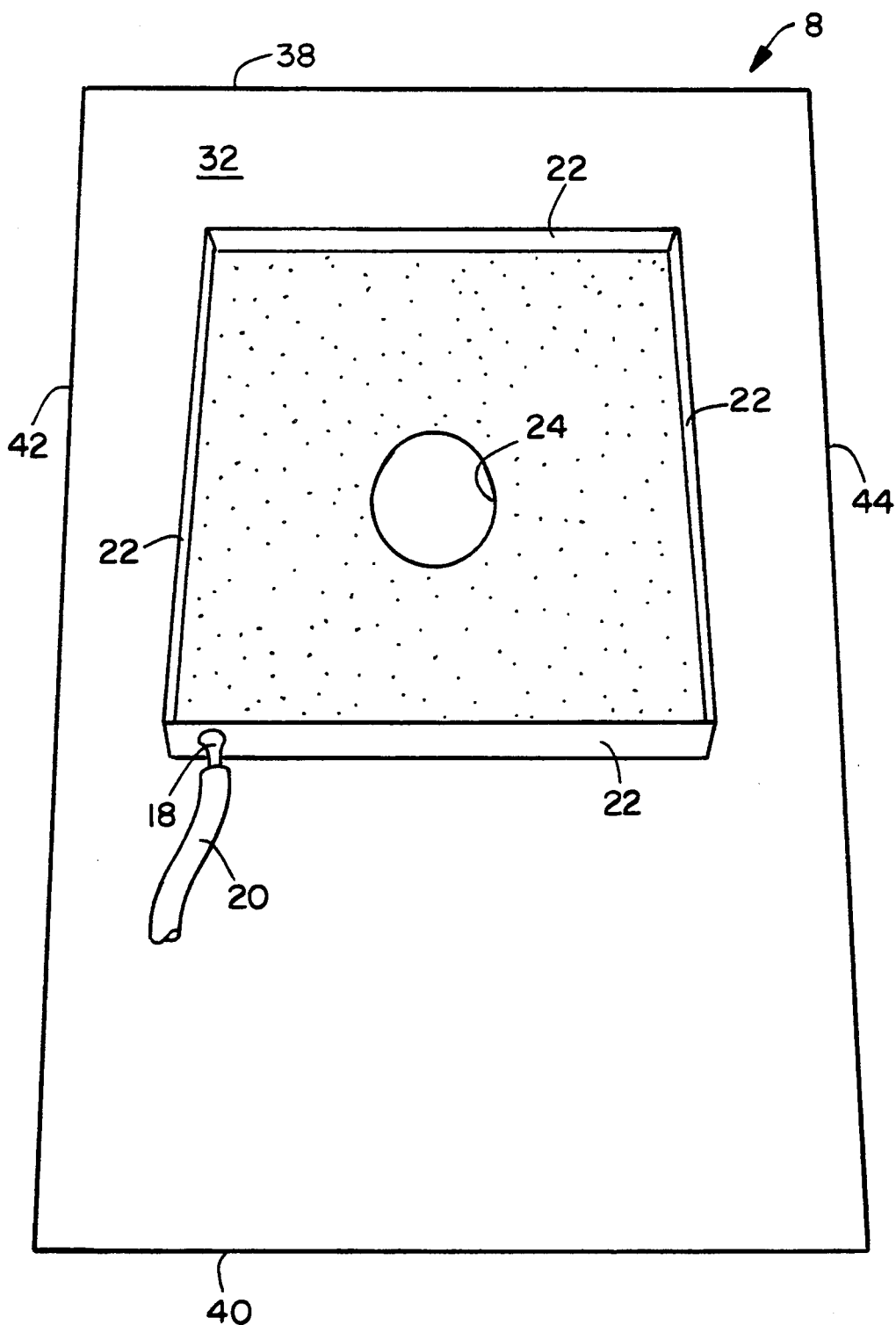
FIG. 6 is yet another embodiment of a fluid evacuation system according to the present invention.

FIG. 6 shows a compact fluid evacuation system 8 according to the present invention wherein the fluid receiving chamber completely surrounds the fenestration 24 and may be used, if desired, with optional fluid control rails 22.

Turning to FIGS. 1 and 3 in more detail there is shown a fluid collection system 8 which includes a liquid permeable top layer 10 and a liquid impervious bottom layer 12 joined to each other by a liquid impervious seal 13 to define a fluid receiving chamber 14 between the top and bottom layers 10 and 12 respectively. The liquid impervious bottom layer 12 may be made from any material which will not readily pass liquids. Plastic films and in particular those films which can be adhesively, ultrasonically or thermally bonded provide desirable materials for forming the liquid impervious bottom layer 12. The liquid permeable top layer 10 may be a single layer or a laminate. Suitable materials include perforated plastic films, nonwoven materials and foamed materials. In addition, laminates may be formed from one or more of the foregoing materials. For example, a perforated plastic film may be laminated to or simply placed in contact with a woven, nonwoven or foamed material which can both absorb and pass fluids through to the perforations in the plastic film below. Such a layer above the perforated plastic film provides the added advantage of acting as a temporary reservoir for the fluids which contact the top layer 10 before the fluids are actually drawn through the top layer 10 and into the fluid receiving chamber 14. In addition, typically hydrophobic materials such as polypropylene spunbond nonwovens may be treated with surfactants to increase the penetration rate of the liquid through the top layer 10. It also should be noted that when using a plastic film, the film may either be perforated across its entire surface or selectively perforated in specific areas to create localized areas of suction.

Given the nature of the materials used to form the top and bottom layers 10 and 12 of the fluid evacuation system 8, these materials will tend to collapse upon themselves when placed under a vacuum. As a result, there is provided within the fluid collection chamber 14 one or more separation means 16 to prevent the collapse of the fluid collection chamber 14 and a reduction in the fluid handling capacity of the fluid evacuation system 8. The separation means 16 may be made from any type of rigid or semi-rigid material and can be either porous or non-porous. For example, rubber blocks or tubing may be used for the separation means 16. In addition, the separation means may be made from an open or closed-cell foam. The foam can be placed within the fluid collection chamber 14 in any number or variety of forms including strips, blocks or an entire layer if the foam itself is capable of transporting liquids. In FIG. 3, the separation means 16 is shown as separate pieces of fluid pervious foam separated by open areas 17 within the chamber 14.

To enable the fluid collection chamber 14 to be evacuated of the fluids which enter the chamber via the liquid pervious top layer 10, the fluid chamber 14 is supplied with an evacuation means 18 which can be used in conjunction with a vacuum pump, fluid reservoir canister and filter (not shown). In FIG. 1, the evacuation means is simply a tapered fluid exit port which provides a path of fluid flow from within the chamber 14 to outside the chamber 14. The evacuation means 18 may be connected to a suction hose 20 which is in turn connected to an evacuation pump system (not shown). As a result, the evacuation means 18 can be regarded as simply the fluid port or the fluid port in conjunction with the entire evacuation system which is used to draw the fluids through the top layer 10 into the fluid chamber 14 and out the fluid port 20.

To better control excessive liquid flow onto the fluid evacuation system 8, the system 8 may be provided with fluid channeling rails 22 about one or more edges of the system 8. Most typically these rails 22 include a fluid impervious material and are attached about the periphery 13 of the system.

Turning to FIGS. 2 and 4, there is shown an alternate embodiment of the present invention in the form of a fluid evacuation rail 30. Essentially, this version of the present invention is a fluid collection rail which has the same components as the fluid evacuation system 8 but which is capable of being molded and then attached to a surgical drape 32 in the expected path of fluid run-off. The drape or mainsheet 32 can be defined as having a top edge 38 and a bottom edge 40 separated by opposed side edges 42 and 44.

In FIG. 2, the fluid rail 30 is formed into a curved configuration and then attached to the drape 32 such that the pad portion extends upwardly away from the plane of the drape 32 so as to trap fluids which can then be suctioned away from the operating site. In FIG. 4, the fluid rail 30 is shown in cross-section attached to the drape 32 via an adhesive 36 located on the attachment means 34. The adhesive in turn can be covered by a release sheet, not shown, as is common practice to protect the adhesive prior to attachment to a drape or patient. Alternatively, the fluid rail 30 may be thermally or ultrasonically bonded to the surgical drape 32 or may be attached via other means readily known to those skilled in the art. As with the other embodiments, the fluid rail 30 includes a liquid pervious top layer 10 and a liquid impervious bottom layer 12 which are sealed about their peripheries 13 to form a fluid receiving chamber 14 including separation means 16. To secure the fluid suction rail 30 to the drape 32 the fluid suction rail 30 is provided with attachment means 34 such as a plastic film or other material which may be affixed to the surgical drape 32. In the embodiment shown in FIG. 4, the attachment means, which in this case is a plastic film, has an additional layer of foam 35 secured to its top surface to absorb at least some of the liquid prior to its being drawn into the fluid collection chamber 14 via the liquid pervious top layer 10. To maintain the fluid suction rail 30 at an angle which is raised above the plane of the drape 32, the fluid suction rail 30 may be provided with support means 37. In FIG. 4, the fluid suction rail 30 is shown as being generally at right angles to the plane of the drape 32, however, by using support means such as malleable metal strips, the fluid suction rail may be positioned at virtually any angle to the drape 32 to better channel and collect fluids.

In use, as fluid leaves the fenestration site 24 and flows toward the fluid suction rail 30, a suction hose 20 can be attached to the evacuation means 18 to create a vacuum within the fluid chamber 14 thereby drawing liquids through the liquid pervious top layer 10 into the fluid chamber 14 and then out of the system via the evacuation means 18 to thereby evacuate fluids from the surgical site.

Turning to FIG. 5, there is shown a fluid evacuation system 8 which includes a fenestration material 21 such as a plastic film with a fenestration 24 defined therein. This portion of the system 8 is placed directly over the incision site and the incision in the patient (not shown) is made through the fenestration 24. Directly below the fenestration material and connected thereto are two separate suction pads 9A and 9B respectively. Each of these suction pads 9A and 9B each have the same configuration as shown in FIG. 1 including a liquid pervious top layer 10, a liquid impervious bottom layer 12 joined to the liquid pervious top layer 10 about the periphery 13. Located within the fluid collection chamber 14 is separation means 16 and the respective suction pads 9A and 9B are provided with evacuation means 18A and 18B respectively. To further channel and contain fluids, the system 8 may be provided with fluid collection rails 22 about one or more edges of the system 8 by attachment to the periphery 13.

In use, either one or the other or both of the suction pads 9A and 9B may be connected to a vacuum source (not shown) via evacuation means 18A and 18B respectively. This system is particularly useful when the vacuum source is not very strong, since the vacuum is being drawn over a reduced area due to the separation of the suction pad into individual compartments, greater suction force is available to quickly remove the fluids.

In FIG. 6, like numerals are used to denote like elements of the present invention. Here again the system 8 is attached to a mainsheet 32 having a top edge 38 and a bottom edge 40 joined by opposed side edges 42 and 44. As can be seen from FIG. 6, in this embodiment, the fluid evacuation system 8 defines a fenestration 24 located within and surrounded by the fluid evacuation system 8. The fenestration 24 is in vertical registry with a similar fenestration in the mainsheet 32. Once again the system 8 may be provided with one or more fluid channeling rails 22 located about the periphery 13 of the system 8. This configuration is particularly well suited for placement directly over the incision site and when connected to a vacuum source via the evacuation means 18 will serve to collect and withdraw fluids within a 360° radius of the site of the incision (not shown).

If desired, the fluid channeling rails can be made into fluid evacuation systems which are in fluid communication with the overall system. In this way, the rails are themselves capable of receiving liquids which can then be evacuated through the main system.

It should be appreciated that each of the systems described in FIGS. 1 through 6 are illustrative only and therefore not intended to limit the scope of the present invention. It also should be noted that these systems can be used by themselves or they can be placed upon or attached to surgical drapes to further facilitate the removal of liquids during a surgical procedure. Lastly, while the present invention has been described in conjunction with its use with surgical drapes, other applications are intended to be within the scope of the present invention. Having thus described the invention in detail, it should be apparent that various modifications and changes can be made to the present invention without departing from the spirit and scope of the following claims.

I claim:

1. A liquid evacuation system comprising:
    a liquid impervious bottom layer and a liquid pervious top layer, said top and bottom layers being joined to each other by a liquid impervious seal to define a liquid receiving chamber between said top and bottom layers;
    separation means located within said chamber for maintaining said top and bottom layers generally separated from one another, and
    means for evacuating said chamber of liquid entering said chamber through said liquid pervious top layer.

2. The system of claim 1 wherein said separation means is a liquid permeable material.

3. The system of claim 2 wherein said liquid permeable material is an open-celled foam.

4. The system of claim 1 wherein said evacuation means is a liquid outlet port for allowing drainage of liquid collected within said chamber.

5. The system of claim 1 which further includes liquid control rails located about at least a portion of the periphery of said top layer and extending above the general plane of said top layer for channeling and retaining liquids on said top layer.

6. The system of claim 5 wherein said liquid control rails are in liquid communication with said liquid receiving chamber and are themselves capable of receiving liquids.

7. The system of claim 1 which further includes attachment means for securing said evacuation system to a surgical drape or patient.

8. The system of claim 7 wherein said attachment means comprises an adhesive on the side of the bottom layer disposed away from said chamber, said adhesive being covered by a release sheet to protect said adhesive prior to the attachment of said system to a drape or patient.

9. The system of claim 1 wherein said liquid permeable top layer is also liquid absorbent to collect and retain liquid prior to its passage into said liquid receiving chamber.

10. The system of claim 1 wherein said top layer has selected areas of liquid permeability and impermeability.

11. The system of claim 1 wherein said top layer comprises a first layer of liquid absorbent and permeable material in contact with a second layer of perforated polymeric film, said first layer being disposed away from said liquid receiving chamber.

12. The system of claim 1 wherein said liquid receiving chamber is compartmentalized into a plurality of chambers each of which has its own evacuation means so that selective liquid evacuation can take place.

13. The system of claim 1 wherein said means for evacuating said chamber of liquids includes a vacuum pump to draw liquids from said receiving chamber.

14. A liquid evacuation system comprising:
    a liquid impervious bottom layer and a liquid absorbent and permeable top layer, said top and bottom layers being joined to each other by a liquid impervious seal to define a liquid receiving chamber between said top and bottom layers;
    separation means located within said liquid receiving chamber for maintaining said top and bottom layers generally separated from one another, said separation means further being liquid permeable;
    liquid control rails located about at least a portion of the periphery of said top layer and extending above the general plane of said top layer for channeling and retaining liquids on said top layer;
    means for evacuating said chamber of liquid entering said chamber through said liquid pervious top layer; and
    attachment means for securing said system to a surgical drape or patient.

15. A surgical drape for collecting liquids comprising:
    a mainsheet having a top edge and a bottom edge separated by opposite side edges, said mainsheet further defining a fenestration therein, and a liquid evacuation system attached to said mainsheet in the expected path of fluid run-off, said system including:
    a liquid impervious bottom layer and a liquid pervious top layer, said top and bottom layers being joined to each other by a liquid impervious seal to define a liquid receiving chamber between said top and bottom layers;
    separation means located within said chamber for maintaining said top and bottom layers generally separated from one another;
    means for evacuating said chamber of liquid entering said chamber through said liquid pervious top layer;
    liquid control rails located about at least a portion of the periphery of said top layer and extending above the general plane of said top layer for channeling and retaining liquids on and said top layer; and
    attachment means for securing said evacuation system to said mainsheet.

16. The drape of claim 15 wherein said liquid evacuation system completely surrounds said fenestration in said mainsheet.

* * * * *